US005417652A

United States Patent [19]

Scott, Sr.

[11] Patent Number: 5,417,652

[45] Date of Patent: May 23, 1995

[54] DEVICE AND METHOD FOR ADMINISTERING FLUID TO THE NOSE

[76] Inventor: Jack J. Scott, Sr., P.O. Box 248, Bethany, Ill. 61914

[21] Appl. No.: 167,241

[22] Filed: Dec. 15, 1993

[51] Int. Cl.[6] .............................................. A61M 16/00

[52] U.S. Cl. ....................................................... 604/19

[58] Field of Search ..................... 604/19; 128/207.13, 128/206.18, 195, 198, 187

[56] References Cited

U.S. PATENT DOCUMENTS 781,516 1/1905 Guthrie ......................... 128/207.13

815,510 3/1906 Coburn .......................... 128/207.13

2,295,321 9/1942 Anderson ....................... 128/206.18

4,216,769 8/1980 Grimes .......................... 128/207.13

*Primary Examiner*—C. Fred Rosenbaum

*Assistant Examiner*—Manuel Mendez

*Attorney, Agent, or Firm*—Senniger, Powers, Leavitt & Roedel

[57] ABSTRACT

A device and method for washing, irrigating or administering fluid to one's nose. The device is a cup with an opening in the side for insertion of the nose. Fluid in the cup is sucked into the nose by inhaling.

10 Claims, 1 Drawing Sheet

DEVICE AND METHOD FOR ADMINISTERING FLUID TO THE NOSE

BACKGROUND OF THE INVENTION

This invention relates to a device for holding fluid and administering fluid to the nose. The fluid may be for washing or irrigating the nasal cavity or may be a medicinal preparation for treating a condition by ingestion through the nose. The invention also relates to a method for irrigating and washing the nasal cavity and for ingesting a medicinal preparation through the nose.

In the treatment of certain conditions, especially conditions affecting the nasal cavities and nasal passages, it is desirable to wash, irrigate, and/or apply a fluid medicinal preparation to the nasal cavities and passages. Heretofore this has been accomplished by use of a spray bottle or similar device which is squeezed in order to force fluid contents of the bottle out of the bottle through a nozzle up into the nose. One drawback of this method is that the amount of fluid administered to the nose is not precisely determinable. Another drawback is that some of the fluid administered to the nose may flow from the nose and onto the face of the patient. Furthermore, the fluid can cause the contents of the nose such as nasal mucus to similarly flow from the nose onto the patient. A further disadvantage is the risk of irritation or injury to the nasal cavity by insertion of a nozzle or other applicator device therein.

SUMMARY OF THE INVENTION

It is an object of this invention to provide a device and method for washing, irrigating, and administering fluid to the nose. It is an object of this invention to provide such a device and method which are adapted for administering predetermined volumes of medicinal preparation to the nose. It is an object of this invention to provide such a device and method which facilitate cleaning, irrigating, and treating the nasal cavities as safely and with as little mess as possible.

Briefly, the invention is directed to a device for administering fluid to the nose. The device is a cup for holding the fluid to be administered. The cup has a bottom wall, a side wall, and a rim. There is an opening in the side wall for inserting one's nose into the cup through the side wall while both the cup and nose are maintained in generally upright position.

The invention is also directed to a method for irrigating, washing, or administering fluid to a nose. A cup containing fluid is positioned in front of a nose. The cup has an opening in its side wall for inserting the nose into the cup through the side wall while both the cup and nose are maintained in generally upright position. The nose is inserted into the cup through the opening in the side wall. The fluid from the cup is inhaled into the nose.

Other objects and features of the invention will be in part apparent and in part pointed out hereinafter.

BRIEF DESCRIPTION OF THE DRAWINGS

Corresponding parts are designated by corresponding reference numerals throughout the several views of the drawings.

DETAILED DESCRIPTION OF THE INVENTION

Figure 1:
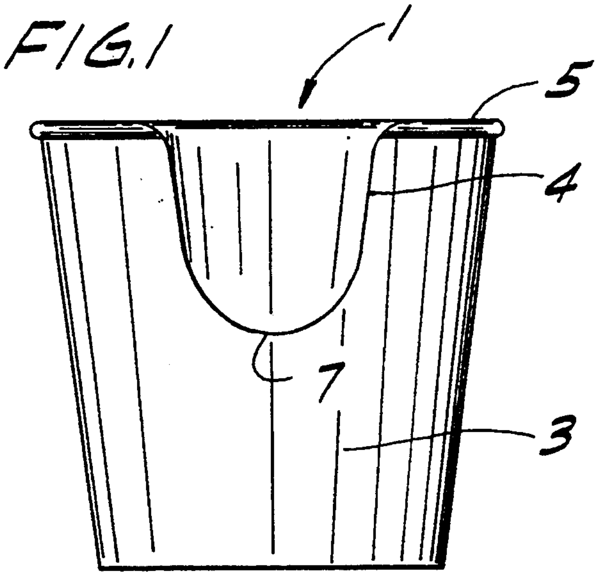
FIG. 1 is a side view of the device of the invention.

Referring now to FIG. 1, a device of this invention is shown generally at 1. The device is a cup having a side wall 2 and bottom wall 3 which define a container for holding a fluid to be administered to the nasal cavity.

The cup has an opening 4 which extends from the rim 5 downwardly toward the bottom of the cup. Rim 5 is preferably beaded or rolled as shown in the figures. The beading or rolling preferably extends completely around the rim and down along the edge of the cup which defines opening 4.

Figure 4:
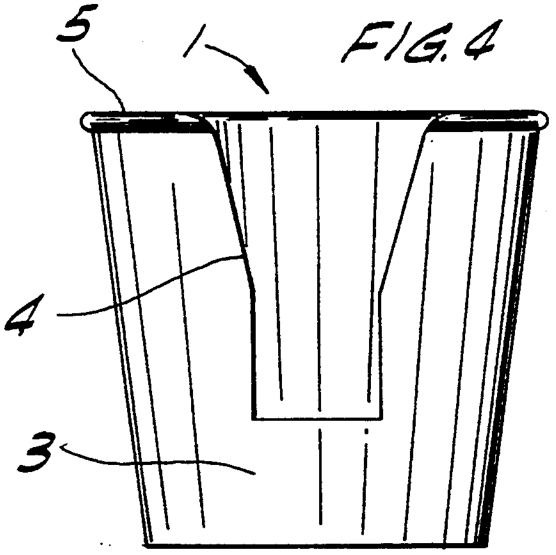
FIG. 4 is a side view of an alternative embodiment of the device of the invention.

Opening 4 is configured to allow the nose to be inserted into the cup such that the edge of the cup which defines the opening closely surrounds the nose. The opening is configured so that, upon pressing of the cup against the face with the nose inserted through the opening, the edge of the opening generally conforms to the contour of the face surrounding the nose to facilitate sealing of the face from the contents of the cup and from material expelled from the nose. In the preferred embodiment, the opening is U-shaped, as shown in FIGS. 1 or 4. The opening may also be V-shaped, rectangular or another shape which permits insertion of the nose therethrough and which conforms generally to the contour of the face surrounding the nose. The depth of the cup from the bottom of the opening 7 to the bottom of the cup is sufficient to hold the desired volume of fluid for washing, irrigating or medicinally treating the nose.

Figure 2:
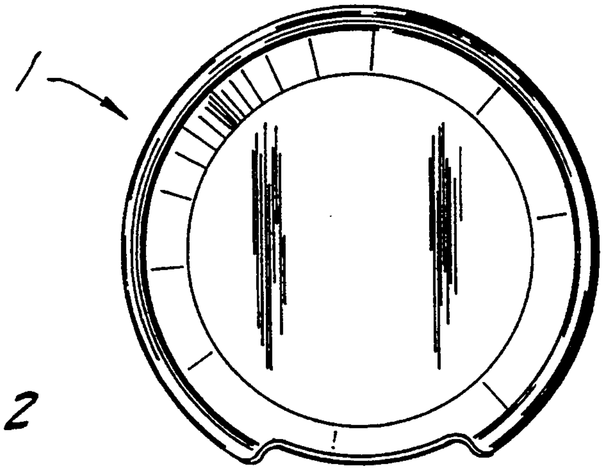
FIG. 2 is a top view of the device of the invention.
Figure 3:
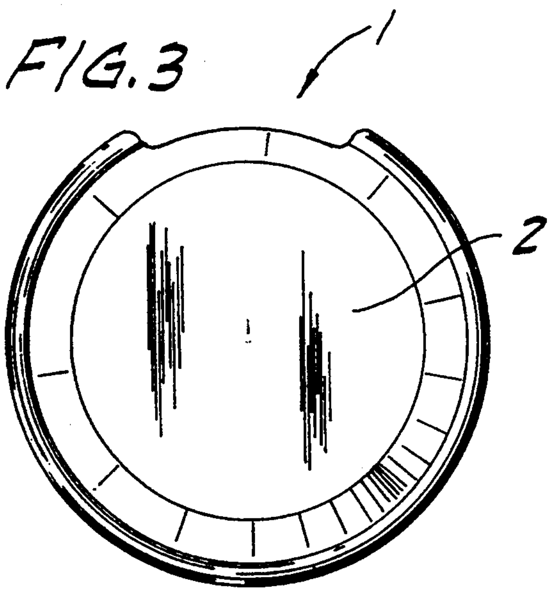
FIG. 3 is a bottom view of the device of the invention.

As shown in FIGS. 2 and 3, the cup is preferably round. However, the cup may be square, rectangular, or another shape capable of retaining fluid. The cup has a volume below the bottom 7 of the opening which holds a predetermined and selected quantity or dosage of fluid for washing, irrigating or treating the nose. This volume is preferably between about 1 and 7 fluid ounces, more preferably between about 2.5 and 4.5 ounces.

In the preferred embodiment as shown where the cup is round, it has a preferred diameter between about 2.5 and 4.5 inches, more preferably between 2.75 and 3.75 inches. The cup has a preferred height between about 2.25 and 3.25 inches, more preferably between 2.5 and 3 inches. The cup has a preferred bottom diameter between about 1.5 and 3 inches, more preferably between 2 and 2.75 inches. The opening in the cup side wall is preferably U-shaped and between about 1 and 2 inches wide at its widest point. The most preferred embodiment of the cup has a top diameter of 3.25 inches, a height of 2.875 inches, a bottom diameter of 2.375 inches, and a U-shaped opening which is about 1.5 inches wide at its widest point and extends to a depth of about 1.25 inches from the upper rim. The cup may be made of paper, plastic, metal, glass or any other material which can be readily manufactured in the desired shape and which is sufficiently sturdy to hold fluid.

In accordance with the method of this invention, fluid is poured into cup 1 to a level which is near the bottom 7 of opening 4. The type of fluid will depend on the application for which the device is used. The fluid may be a saline solution, special cleansing formula or medicinal fluid.

The cup is positioned near a patient's nose and the patient's head and nose and the cup are maintained in their normal upright positions. The patient's nose is inserted into the cup through opening 7. The cup is gently pressed against the patient's face to provide a seal between the face and the interior of the cup. The bottom of the patient's nasal septum may be rested on the bottom of opening 7. If the cup is not filled with fluid all the way up to the bottom 7 of opening 4, the cup may be tilted slightly toward the patient's face such that the fluid approaches the bottom 7 of the opening. The patient then inhales with sufficient force to cause the fluid in the cup to be ingested into the nasal cavities and, if desired, into and through the nasal passages.

In one preferred embodiment of the method, where it is desirable to wash or irrigate the nasal cavity, the patient inhales with sufficient force to cause the treating fluid from the cup to be sucked into and maintained in the nasal cavities, but not with sufficient force that the fluid is sucked into and through the nasal passages. If desired, once fluid is brought into the nasal cavities, the cup may be moved such that the fluid line therein is not in contact with the nose so that air may be breathed in through the nose to facilitate cleansing or irrigation by agitation of the fluid in the nasal cavities. After fluid is maintained in the nose for a sufficient period, usually a few seconds, to provide the desired amount of cleansing or irrigation, the fluid and loose contents of the nose, which may include nasal mucus, blood, nose hair and dirt, are expelled from the nose into the cup by outward blowing through the nose. Advantageously, the cup is configured so as to receive the contents blown from the nose and to protect the face from such contents. As an optional additional step, the patient may close one nostril by pressing with a thumb and expel material from the other nostril by exhaling therethrough with increased force. The process may be repeated one or more times if desired.

In an alternative embodiment of the method of the invention, the fluid in the cup is a medicinal preparation for treating a sinus condition or other condition to be treated by inhaling of liquid or mist through the nasal passage. According to this method, fluid from the cup is inhaled with greater force than in the above method so that it is sucked into and, if desired, through the nasal passages.

In view of the above, it will be seen that the several objects of the invention are achieved and other advantageous results attained.

As various changes could be made in the above construction and methods without departing from the scope of the invention, it is intended that all matter contained in the above description or shown in the accompanying drawings shall be interpreted as illustrative and not in a limiting sense.

What is claimed is:

1. A device for administering liquid comprising a saline solution, a special cleansing formula, or a medicinal fluid to the nose comprising a cup for holding the liquid to be administered, the cup having a bottom wall, a side wall, and a rim, the device further comprising a nasal opening in the sidewall opening in the side wall for inserting a nose into the cup through the side wall while both the cup and nose are maintained in generally upright position, the side wall having no other opening therein from one side of said nasal opening to the other side of said nasal opening for holding the liquid to be administered to the nose.

2. The device of claim 1 wherein the nasal opening extends from the rim downwardly along the side wall toward the bottom wall.

3. The device of claim 2 wherein the nasal opening is U-shaped.

4. The device of claim 1 comprising a liquid in the cup.

5. A method for irrigating, washing, or administering liquid to a nose comprising the steps of:

positioning a cup containing liquid in front of the nose, the cup having an opening in a side wall for inserting the nose into the cup through the side wall while both the cup and nose are maintained in generally upright position;

inserting the nose into the cup through the opening in the side wall; and inhaling the liquid in the cup into the nose.

6. A device for administering liquid comprising a saline solution, a special cleansing formula, or a medicinal fluid to a nose comprising a cup for holding the liquid to be administered, the cup having a bottom wall, a side wall, and a rim, the device further comprising an opening in the side wall for inserting the nose into the cup through the side wall while both the cup and nose are maintained in generally upright position, the opening having a bottom which is positioned on the side wall such that the depth of the cup from the bottom of the opening to the bottom of the cup is sufficient to hold between about 1 and 7 fluids ounces of liquid in the cup.

7. The device of claim 6 wherein the depth of the cup from the bottom of the opening to the bottom of the cup is sufficient to hold between about 2.5 and 4.5 fluid ounces of liquid in the cup.

8. The device of claim 6 wherein the cup has a height between about 2.25 and 3.25 inches.

9. The device of claim 8 wherein the cup has a height between about 2.5 and 3.5 inches.

10. The device of claim 9 wherein the cup has a top diameter between about 2.75 and 3.75 inches, a bottom diameter between 2 and 2.75 inches, and wherein the opening in the cup side wall is U-shaped and between about 1 and 2 inches wide at its widest point.

* * * * *